United States Patent [19]

Chester et al.

[11] Patent Number: 4,594,146

[45] Date of Patent: * Jun. 10, 1986

[54] CONVERSION WITH ZEOLITE CATALYSTS PREPARED BY STEAM TREATMENT

[75] Inventors: Arthur W. Chester; Yung-Feng Chu, both of Cherry Hill, N.J.

[73] Assignee: Mobil Oil Corporation, New York, N.Y.

[*] Notice: The portion of the term of this patent subsequent to Jan. 31, 2001 has been disclaimed.

[21] Appl. No.: 685,194

[22] Filed: Dec. 21, 1984

Related U.S. Application Data

[63] Continuation-in-part of Ser. No. 539,497, Oct. 6, 1983, Pat. No. 4,522,929, which is a continuation-in-part of Ser. No. 346,440, Feb. 8, 1982, Pat. No. 4,429,176.

[51] Int. Cl.⁴ .................... C10G 11/05; C10G 45/10; C10G 47/18; C10G 47/20
[52] U.S. Cl. ................................ 208/111; 208/120; 502/55
[58] Field of Search .................. 208/111, 120; 502/55, 502/77

[56] References Cited

U.S. PATENT DOCUMENTS

| | | | |
|---|---|---|---|
| 3,965,209 | 6/1976 | Butter et al. | 208/DIG. 2 |
| 4,188,282 | 2/1980 | Tabak et al. | 208/134 |
| 4,224,141 | 9/1980 | Morrison et al. | 208/134 |
| 4,236,996 | 12/1980 | Tabak et al. | 208/134 |
| 4,259,170 | 3/1981 | Graham et al. | 208/33 |
| 4,326,994 | 5/1982 | Haag et al. | 502/77 |
| 4,400,265 | 8/1983 | Shen | 208/97 |
| 4,429,176 | 1/1984 | Chester et al. | 585/481 |

Primary Examiner—Andrew H. Metz
Assistant Examiner—O. Chaudhuri
Attorney, Agent, or Firm—Alexander J. McKillop; Michael G. Gilman; Dennis P. Santini

[57] ABSTRACT

A zeolite of improved stability for use in acid-catalyzed reactions is prepared by mildly presteaming the catalyst under controlled conditions of temperature, time, and steam partial pressure. The resulting catalyst retains nearly the same activity as that of a fresh unsteamed catalyst.

20 Claims, 4 Drawing Figures

CONVERSION WITH ZEOLITE CATALYSTS PREPARED BY STEAM TREATMENT

CROSS REFERENCE TO RELATED APPLICATIONS

This application is a continuation-in-part of U.S. Ser. No. 539,497, filed on Oct. 6, 1983, now U.S. Pat. No. 4,522,929 which is a continuation-in-part of application Ser. No. 346,440, filed on Feb. 8, 1982, now U.S. Pat. No. 4,429,176, the entire contents of both of which earlier applications are incorporated herein by reference.

BACKGROUND OF THE INVENTION

1. Field of the Invention

This invention relates to a process for presteaming a zeolite catalyst so as to substantially retain its initial activity and to a process for the preparation of superior zeolite catalysts to be used in acid-catalyzed reactions.

2. Description of the Relevant Art

Acid-catalyzed reactions, e.g., xylene isomerization, toluene disproportionation, etc., result in the rapid degeneration of catalyst activity. It is well known to the art that mild-to-severely steamed zeolite catalysts provide improved stability but suffer from lowered activity in acid-catalyzed reactions.

Much of the prior art in this area deals with severely steamed zeolite catalysts in reactions such as xylene isomerization.

U.S. Pat. No. 4,224,141 discloses a xylene isomerization process with a catalyst steamed at a temperature in excess of 538° C. (1000° F.) for a period of time longer than 15 hours. The resulting catalyst is highly stable, but suffers from lowered activity.

U.S. Pat. No. 4,188,282 discloses a xylene isomerization process using a catalyst with a silica/alumina ratio of at least 200. The catalyst is severely steamed to a lowered activity as described in U.S. Pat. No. 4,016,218 and U.S. Pat. No. 3,965,209.

U.S. Pat. No. 4,236,996 discloses a xylene isomerization process wherein the catalyst is steamed at a high temperature to reduce the activity such that the conversion reaction temperature must be increased by at least 10° C. (50° F.) to equal the conversion capability of an unsteamed zeolite.

U.S. Pat. No. 3,965,209 discloses a process whereby the zeolite is steamed to reduce the alpha activity to less than 500 by treating the zeolite in a steam atmosphere at a temperature of from 250° C. to about 1000° C. (526° F. to about 2026° F.) for from about ½ hour to 100 hours.

U.S. Pat. No. 4,326,994 discloses a process whereby a zeolite is steamed to activate or increase its alpha activity.

Other important acid catalyzed reactions include various cracking reactions, such as fluidized catalytic cracking, or hydrocracking. Of special interest in hydrocracking is catalytic hydrodewaxing of distillates and lubricant stocks.

Fluidized catalytic cracking is a well-known commercial refining process. More details of the fluidized catalytic cracking process are disclosed in U.S. Pat. No. 4,309,279, U.S. Pat. No. 4,309,280 and U.S. Pat. No. 3,758,403, the entire contents of which patents are incorporated herein by reference.

Catalytic hydrocracking, conducted in the presence of relatively high hydrogen partial pressures, with particular emphasis on dewaxing of oils by shape selective cracking is disclosed in U.S. Pat. No. Re 28,398, U.S. Pat. No. 3,956,102, U.S. Pat. No. 3,894,938 and U.S. Pat. No. 4,332,670, the entire contents of which patents are incorporated herein by reference.

As discussed in greater detail in these patents, shape selective cracking of either lubricant stocks or of distillates can be conducted using shape selective catalysts, i.e., those having a constraint index of about 1 to 12.

SUMMARY OF THE INVENTION

Figure 1:
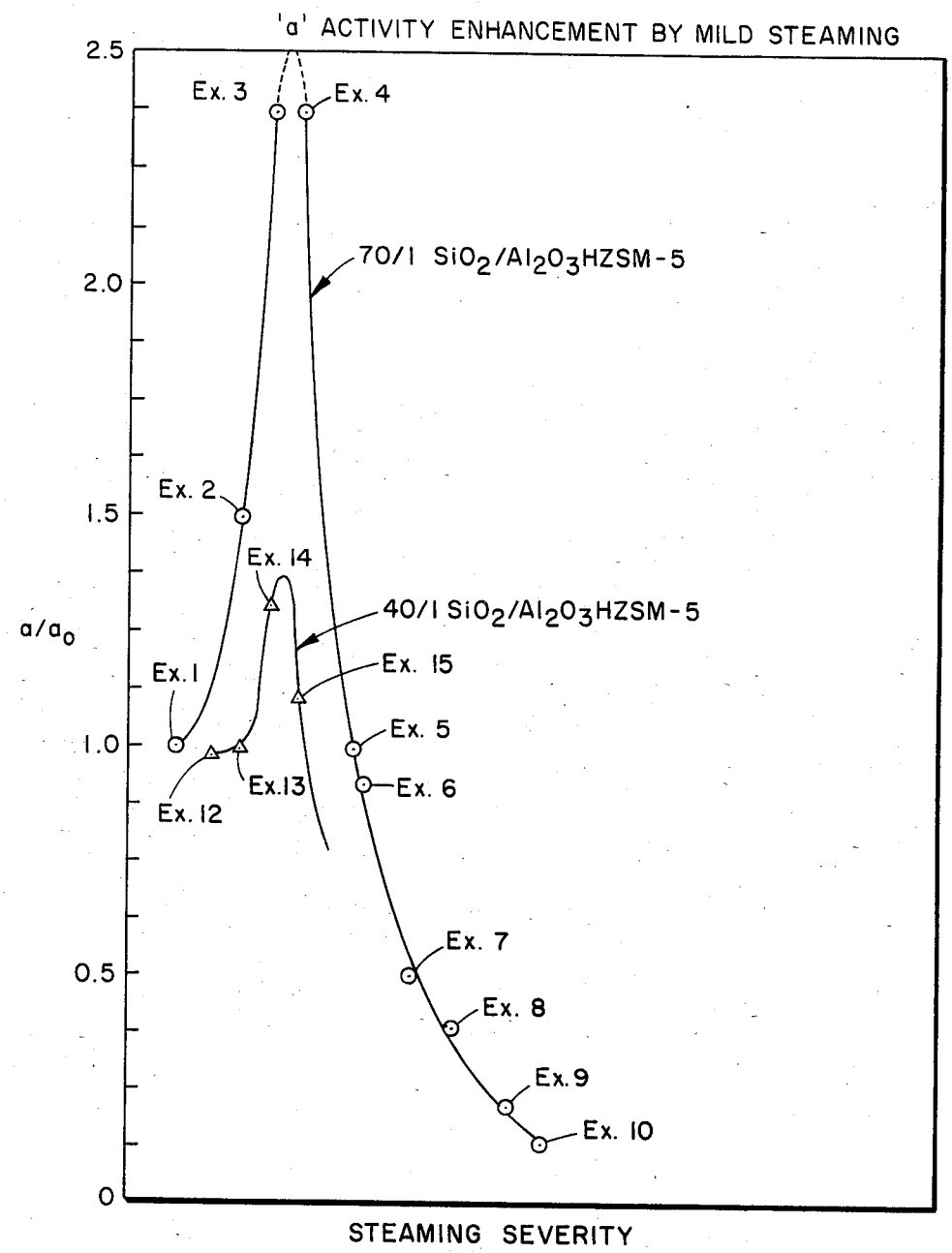
FIG. 1 illustrates the relationship of activity enhancement by mild steaming vs. steaming severity.

Accordingly the present invention provides a process for converting a feedstock comprising hydrocarbon compounds to conversion products comprising hydrocarbon compounds of lower molecular weight than said feedstock hydrocarbon compounds which comprises contacting said feedstock at conversion conditions with a catalyst comprising a zeolite having a silica/alumina ratio greater than 12 and a constraint index of 1 to 12, and wherein said zeolite containing catalyst is steamed in its fresh state under controlled conditions of temperature, time and steam partial pressure so as to initially increase the $\alpha$-activity of said catalyst and produce a steam catalyst having a peak $\alpha$-activity, and subsequently reduce the $\alpha$-activity from said peak $\alpha$-activity to an $\alpha$-activity substantially the same as the $\alpha$-activity of said fresh catalyst and no more than 25% below the initial $\alpha$-activity of said fresh catalyst.

In another embodiment, the present invention provides a process for catalytically dewaxing a heavy oil stock to provide a catalytically dewaxed oil with reduced wax content which comprises contacting said oil at catalytic dewaxing conditions including a temperature of about 450° to 900° F. in a reaction zone in the presence of hydrogen with a catalyst comprising a zeolite having a silica/alumina ratio greater than 12 and a constraint index of 1 to 12, and wherein said zeolite containing catalyst is steamed in its fresh state under controlled conditions of temperature, time and steam partial pressure so as to initially increase the $\alpha$-activity of said catalyst and produce a steamed catalyst having a peak $\alpha$-activity, and subsequently reduce the $\alpha$-activity from said peak $\alpha$-activity to an $\alpha$-activity substantially the same as the $\alpha$-activity of said fresh catalyst and no more than 25% below the initial $\alpha$-activity of said fresh catalyst.

In yet another embodiment, the present invention provides a process for catalytically hydrodewaxing a lubricating oil base stock to provide a catalytically hydrodewaxed lubricating oil base stock with reduced wax content which comprises contacting said stock at catalytic hydrodewaxing conditions including a temperature of about 450° to 900° F. in a reaction zone operating with a hydrogen partial pressure of about 10 to 3000 psia with a catalyst comprising a zeolite having a silica/alumina ratio greater than 12 and a constraint index of 1 to 12, and wherein said zeolite containing catalyst is steamed in its fresh state under controlled conditions of temperature, time and steam partial pressure so as to initially increase the α-activity of said catalyst and produce a steamed catalyst having a peak α-activity, and subsequently reduce the α-activity from said peak α-activity to an α-activity substantially the same as the α-activity of said fresh catalyst and no more than 25% below the initial α-activity of said fresh catalyst.

The present invention also relates to an improved process for the catalytic conversion of an organic reactant involving an acid-catalyzed reaction using a catalyst comprising a zeolite having a silica/alumina ratio greater than 12 and a constraint index of 1 to 12. Such a process comprises subjecting such a zeolite-containing catalyst in its fresh state to a steaming procedure under controlled conditions of temperature, time and steam partial pressure so as to initially increase the α-activity of said catalyst and produce a steamed catalyst having a peak α-activity, and to subsequently reduce the α-activity from said peak α-activity no more than 25% below the initial α-activity of said fresh catalyst. The catalyst, when steamed in this manner, has enhanced stability over the fresh catalyst.

In a preferred invention embodiment, the organic reactant conversion process involves isomerizing the xylene content of a charge mixture of eight carbon atom aromatic hydrocarbon compounds, which mixture contains xylenes and ethylbenzene, by contacting the mixture under conversion conditions with a catalyst comprising a zeolite having a silica/alumina ratio greater than 12 and a constraint index of 1 to 12. Such a xylene isomerization process utilizes such a catalyst which has been steamed in a particular manner while maintaining a conversion temperature of about 260° C. to 538° C. Prior to contact with the charge mixture, the zeolite-based catalyst is steamed at a temperature and pressure and for a period of time so as to initially increase the α-activity of the catalyst and produce a steamed catalyst having a peak α-activity and to subsequently reduce the α-activity from said peak α-activity to an α-activity no less than 75% of the initial α-activity of the fresh, unsteamed zeolite-based catalyst. The catalyst, when steamed in this manner, has enhanced stability over the fresh catalyst.

This invention is accomplished by presteaming a fresh zeolite catalyst under mild conditions until the activity of the mildly steamed catalyst has been increased to a peak and then reduced to a level which is substantially equivalent to that of a fresh, unsteamed catalyst. The siliceous crystalline zeolites used in such catalysts are generally members of a class of zeolites that exhibits unusual properties. Such zeolite materials are those which have a silica to alumina molar ratio of at least 12 and a constraint index within the range of 1 to 12. Zeolite materials of this type are well known. Such zeolites and their use as catalysts for conversion of aromatic hydrocarbons are generally described, for example, in the aforementioned U.S. Pat. No. 4,236,996. Crystalline zeolites of the type useful in the catalysts of the present invention include ZSM-5, ZSM-11, ZSM-12, ZSM-23, ZSM-35, ZSM-38 and ZSM-48, with ZSM-5 being particularly preferred.

ZSM-5 is described in greater detail in U.S. Pat. Nos. 3,702,886 and U.S. Pat. No. Re 29,948, which patents provide the X-ray diffraction pattern of the therein disclosed ZSM-5.

ZSM-11 is described in U.S. Pat. No. 3,709,979, which discloses in particular the X-ray diffraction pattern of ZSM-11.

ZSM-12 is described in U.S. Pat. No. 3,832,449, which discloses in particular the X-ray diffraction pattern of ZSM-12.

ZSM-23 is described in U.S. Pat. No. 4,076,842, which discloses in particular the X-ray diffraction pattern for ZSM-23.

ZSM-35 is described in U.S. Pat. No. 4,016,245, which discloses in particular the X-ray diffraction pattern for ZSM-35.

ZSM-38 is described in U.S. Pat. No. 4,046,859, which discloses in particular the X-ray diffraction pattern for ZSM-38.

ZSM-48 is more particularly described in European Patent Publication No. EP-A-0015132 which includes the X-ray diffraction pattern for ZSM-48.

When synthesized in the alkali metal form, the zeolite used to form the catalysts herein can be conveniently converted in a conventional manner to the hydrogen form, generally by intermediate formation of the ammonium form as a result of ammonium ion exchange and calcination of the ammonium form to yield the hydrogen form of the zeolite. In addition to the hydrogen form, other forms of the zeolite can be employed in the catalyst compositions herein so long as the original alkali metal has been reduced to less than about 50% by weight of the original alkali metal contained in the zeolite as-synthesized, usually 0.5% by weight or less. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In preparing the zeolite-containing catalysts used in the present invention, the above-described siliceous crystalline zeolite material can be combined with an inorganic oxide binder or matrix comprising another material resistant to the temperature and other conditions employed in the organic reactant conversion process embodiments of the present invention. Such matrix material is useful as a binder and imparts greater resistance to the catalyst for the severe temperature, pressure and reactant feed stream velocity conditions encountered in such processes.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the binder for the siliceous crystalline zeolite material employed herein can comprise a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silicamagnesia-zirconia. The matrix may be in the form of a cogel. The relative porportions of zeolite component and inorganic oxide gel matrix, on an anhydrous basis, may vary widely with the zeolite content ranging from between about 1 to about 99 percent by weight and more usually in the range of about 25 to about 80 percent by weight of the dry catalyst.

The zeolite-based catalysts hereinbefore described are known to be useful in promoting a wide variety of organic compound conversion reactions including, for example, processing of aromatic hydrocarbons. U.S. Pat. No. 4,163,028, for instance, describes a method of processing $C_8$ aromatics for isomerization of xylene and conversion of ethylbenzene. According to that patent, the reactions are conducted at temperatures of 427° C. to 537° C. (800° F. to 1000° F.) with a zeolite having a constraint index of 1 to 12 and a very high silica/alumina ratio which may be as high as or higher than 3000. Such catalysts have low acid activity by reason of the small number of sites capable of being rendered protonic by ammonium exchange and calcination.

The improvement over the prior art which forms the basis of the present invention is predicated upon the discovery that it is not necessary to severely reduce the activity of zeolite catalyst by steaming in order to obtain enhanced stability. It has been found that, by mildly presteaming a fresh zeolite catalyst under controlled conditions, the catalyst will initially exhibit an increase in activity followed by a gradual decline. When the activity of the catalyst becomes substantially similar to that of the fresh, unsteamed catalyst, the steam treatment is terminated. The resulting catalyst has an activity level substantially similar to that of fresh, unsteamed catalyst together with improved stability.

EXAMPLES 1-10

Table 1 illustrates the effect of very mild presteaming on fresh zeolite catalyst for use in xylene isomerization. The catalyst employed in each example is HZSM-5 with a silica/alumina ratio of 70. In Table 1, $\alpha$ represents the degree of activity of the mildly steamed catalyst; $\alpha_o$ represents the degree of activity of the fresh, unsteamed catalyst, and $\alpha/\alpha_o$ represents the degree in which $\alpha$ increases over or decreases below $\alpha_o$.

As is well known in the art, the $\alpha$-activity gives an approximate indication of the catalytic cracking activity of the catalyst compared to a standard catalyst and it gives the relative rate constant (rate of normal hexane conversion per volume of catalyst composition per unit time). It is based on the activity of the highly active silica-alumina cracking catalyst taken as an $\alpha$ of 1. This test is described in U.S. Pat. No. 3,354,078 and in *The Journal of Catalysis*, Vol. 4, pp. 522-529, August 1965. For purposes of the present invention, however, all measurements of $\alpha$ are to be made at 538° C. (1000° F.) and all references to $\alpha$ are to be understood to refer to the value obtained when the hexane cracking is measured at 538° C. (1000° F.).

Illustrated in FIG. 1 is the relationship of activity of the mildly presteamed catalyst to the steaming severity of the catalyst. The parameters for steaming severity are represented in Table 1. It is understood that the term "steaming severity" represents a proportional relationship between the length of time, the temperature, the partial pressure and the percent of steam in the steam treatment. As is shown in FIG. 1, an increase in steaming severity resulted in an increase in $\alpha$-activity of the catalyst to a point of peak enhancement (represented by Example 3, Table 1). With continued increases in steaming severity, the $\alpha$-activity decreased. At the level of severity represented by Example 5, Table 1, the $\alpha$-activity of the catalyst was substantially equivalent to that of the fresh catalyst ($\alpha/\alpha°=0.9$). As can be readily seen from Examples 7-10, increased steaming severity further diminished the $\alpha$-activity of the zeolite catalyst.

Figure 2:
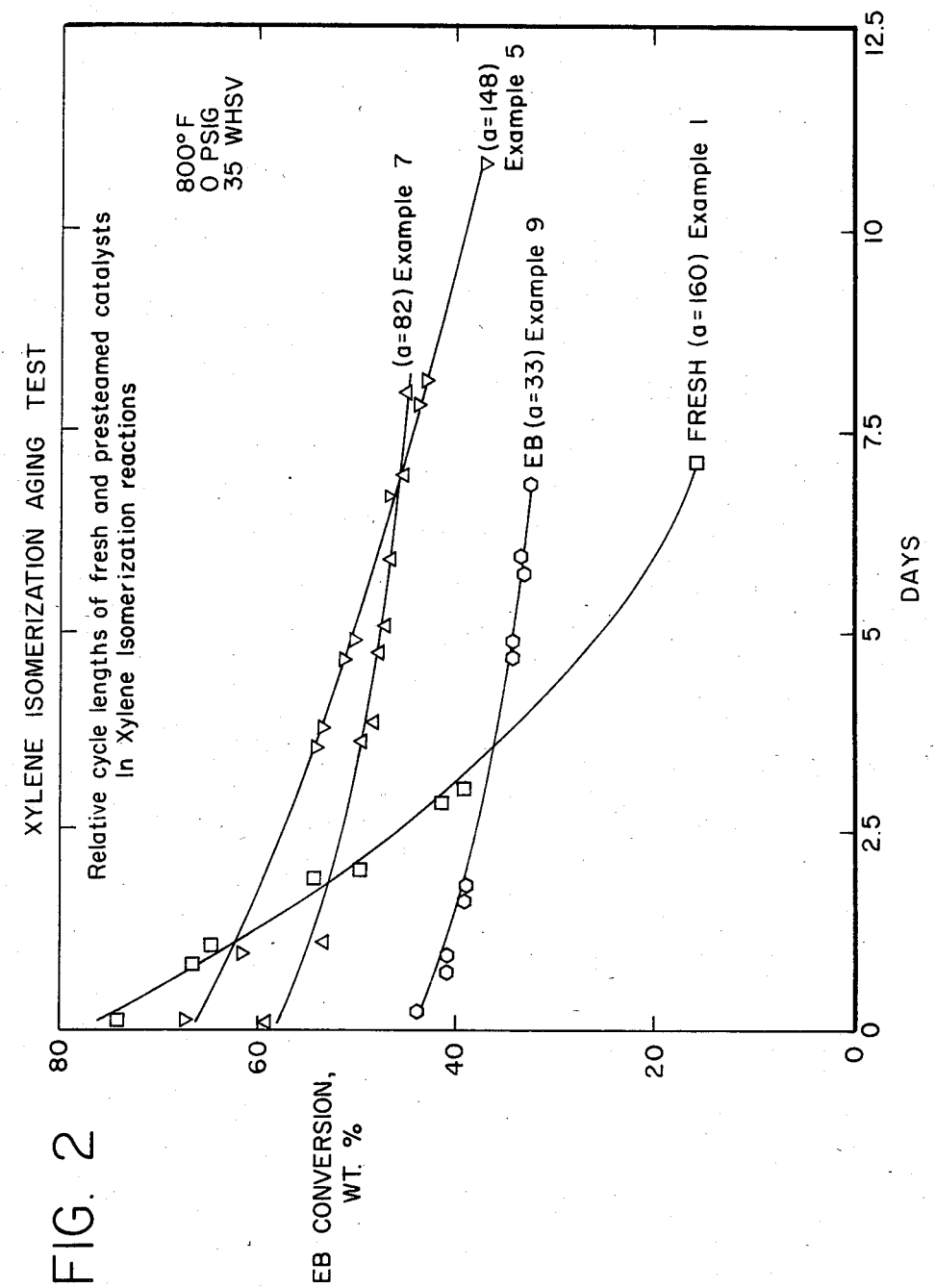
FIG. 2 illustrates the relative cycle lengths of fresh and presteamed catalysts in xylene isomerization reactions.

The import of mildly presteaming a zeolite catalyst is disclosed in FIG. 2 which illustrates the relative cycle lengths of fresh and presteamed catalysts in xylene isomerization reactions. Under similar isomerization conditions, the presteamed catalysts ($\alpha=148$) continued to operate at least 3 times longer per run. As the steaming severity increased (Examples 6-10), the resultant catalysts demonstrated increased stability. However, as is shown in Table 1, the catalyst activity diminished. Thus, mildly steaming a fresh zeolite catalyst under conditions such that the steaming conditions result in a catalyst having an $\alpha$-activity no less than 75% and, preferably, greater than 85% of the activity of a fresh unsteamed catalyst and with greatly enhanced stability is desired for the present invention.

EXAMPLES 11-15

Table 2 and FIG. 1 show the effect of mildly presteaming a zeolite catalyst, e.g., HZSM-5, silica/alumina ratio 40. Such a catalyst is desirable for the conversion of propane to aromatics.

TABLE 1

Effect of Steaming of HZSM-S

| Example No. | 1 | 2 | 3 | 4 | 5 | 6 | 7 | 8 | 9 | 10 |
|---|---|---|---|---|---|---|---|---|---|---|
| Steam Treat | None | 100% | 100% | 100% | 100% | 100% | 100% | 100% | 100% | 100% |
| Hours | Fresh | 6 | 6 | 6 | 3 | 6 | 6 | 8 | 3.5 | 8 |
| Temp. °F. | Fresh | 400 | 500 | 600 | 800 | 800 | 850 | 875 | 1000 | 1025 |
| Press, psig | Fresh | 0 | 0 | 0 | 0 | 0 | 0 | 0 | 0 | 0 |
| $\alpha$ | 160* | 240 | 380 | 360 | 148 | 130 | 82 | 60 | 33 | 20 |
| $\alpha/\alpha_o$ | 1 | 1.5 | 2.4 | 2.3 | 0.9 | 0.8 | 0.5 | 0.4 | 0.2 | 0.1 |

*$\alpha = \alpha_o$

TABLE 2

Effect of Presteaming HZSM-5

| Example No. | 11 | 12 | 13 | 14 | 15 |
|---|---|---|---|---|---|
| Steam Treat | None | 100% | 100% | 100% | 100% |
| Hours | Fresh | 6 | 6 | 6 | 6 |
| Temp. °C. | Fresh | 149 | 204 | 260 | 316 |
| Press. KPa | Fresh | 101 | 101 | 101 | 101 |
| | 550* | 520 | 540 | 740 | 600 |
| $\alpha/\alpha_o$ | 1 | 0.95 | 1.0 | 1.3 | 1.1 |

*$\alpha/\alpha_o$

Figure 3:
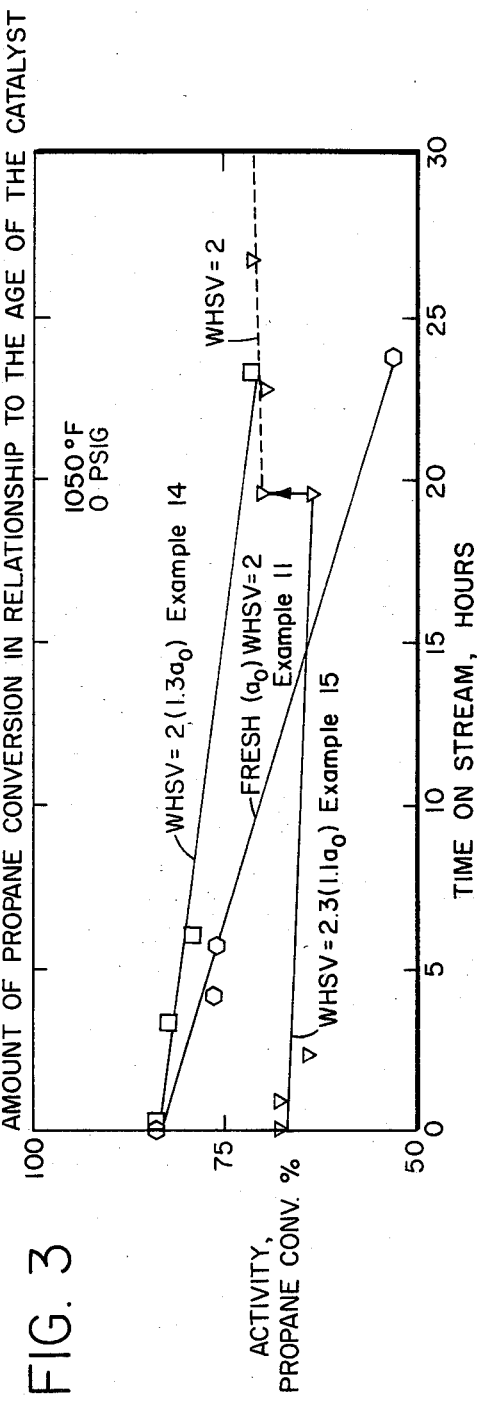
FIG. 3 represents the relationship of the amount of propane conversion to the age of the catalyst.

FIG. 3 represents the relationship of the amount of propane conversion to the age of the catalyst (time on stream) for three catalysts illustrated by Examples 11, 14 and 15 of Table 2. The broken curves represent the conversion level (FIG. 3) and selectivity level (FIG. 4) of the optimally steamed catalyst (Example 15) after its WHSV was changed from 2.3 to 2 and the catalyst remained on stream for an additional 20 hours. Although the initial activity of the optimally steamed catalyst was slightly less than that for either the fresh catalyst (Example 11) or the mildly steam treated catalyst (Example 14), the activity of the optimally steamed catalyst showed greater stability than either of the other catalysts.

Figure 4:
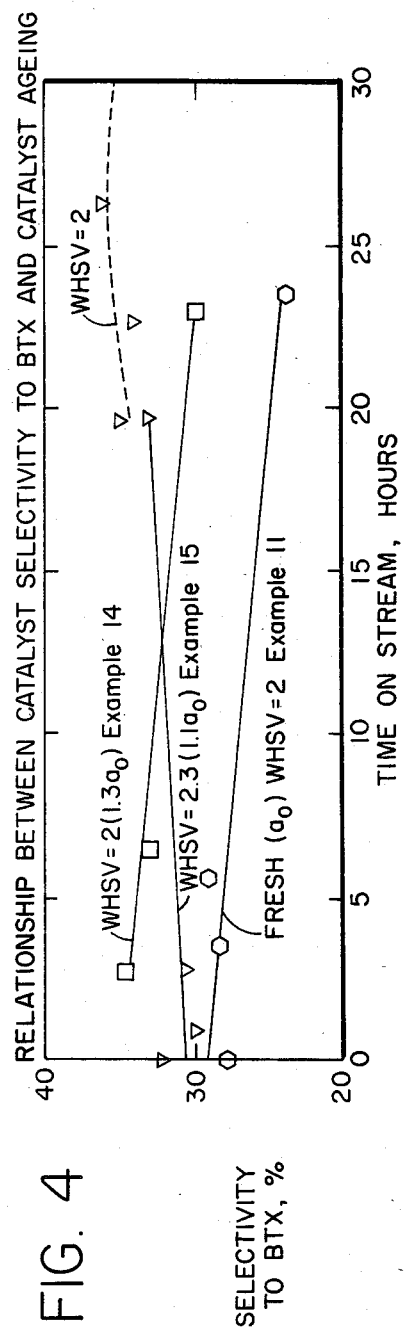
FIG. 4 represents BTX selectivity vs. catalyst age.

FIG. 4 represents the relationship between catalyst selectivity to BTX (Benzene, Toluene, Xylene) and catalyst aging for three catalysts. The selectivity to BTX of the catalyst of Example 15 was greater than that of the fresh catalyst (Example 11). The initial selectivity of the catalyst of Example 14 was slightly greater than the optimally steamed catalyst of Example 15, however, the optimally steamed catalyst shows a greater stability.

The results of these experiments show that mild presteaming of a catalyst to place its $\alpha$-activity past peak enhancement but no less than 75% and, preferably, within 10% of the initial $\alpha$-activity is essential for a highly stable catalyst of high activity and selectivity.

The zeolite catalysts to be steamed according to the invention are generally those zeolites of at least 12 silica/alumina ratio and a constraint index of 1 to 12 which, in the acid form, have activity to convert about 30% of the ethylbenzene in a mixture thereof with xylenes under the isomerization conditions of the aforementioned U.S. Pat. No. 3,856,872, say 316° C.–371° C. (600°–700° F.). The degree of steaming should be such that the $\alpha$-activity of the steamed catalyst should be less than the $\alpha$-activity of the fresh, unsteamed catalyst but no greater than 25% less than the $\alpha$-activity of the fresh catalyst and preferably no greater than 10% less. Under these conditions, the reaction temperature of xylene isomerization reactions should increase by no more than 14° C. (25° F.) to attain the same ethylbenzene conversion as was observed before steaming. The reaction of the present invention will be conducted at such elevated temperatures, above 316° C. (600° F.), as to realize about 30% conversion of the ethylbenzene in the charge. As the temperature is further increased to and above about 343° C. (650° F.) the reaction of ethylbenzene shifts from disproportionation to dealkylation.

The present invention involves using mild temperature presteaming to partially deactivate the catalyst. The deactivation should be conducted to a level such that the steamed catalyst activity is no less than 75% of the activity of the fresh, unsteamed catalyst and the process requires a maximum 14° C. (25° F.) rise in operating temperature, well below the minimum 28° C. (50° F.) rise referred to in U.S. Pat. No. 4,236,996. Additionally, the mildly presteamed catalyst demonstrates superior stability characteristics while maintaining catalytic activity substantially equivalent to that of fresh, unsteamed catalysts.

The major importance of this development relates to the use of zeolite catalysts, particularly ZSM-5, in acid catalyzed reactions, e.g. xylene isomerization, propane conversion to BTX, toluene disproportionation, hydrocracking, dewaxing, conversion of alcohols to hydrocarbons such as methanol to gasoline and/or olefins, synthesis gas conversion to fuels, conversion of olefins to heavier fuels, etc. Such reactions would preferably incorporate a catalyst with the unique qualities of stability and catalytic activity similar to fresh, unsteamed catalysts.

For such uses it is possible to combine the zeolites of the present invention with metal promoters such as Zn, ZnPd, Pt, Cr, etc. Such promoters may be incorporated with the zeolite in accordance with the ion exchange technique described hereinbefore or may be incorporated by other techniques such as impregnation. Incorporation of such metal promoters can occur either before or after the zeolite catalysts are steamed in accordance with the present invention.

DODECANE HYDROCRACKING OVER OPTIMALLY STEAMED ZSM-5

EXAMPLES 16–17

Mild steaming results in an enhancement of alpha activity, but as steaming severity increases, the alpha activity decreases. The optimal steaming of ZSM-5, in accordance with the present invention, results in a catalyst with about the same alpha activity as the starting material, but enhanced stability and higher long term activity. Surprisingly, the optimally steamed material, when used for hydrocracking of dodecane, provides superior catalyst activity (as measured in the plant) and a significant increase in gasoline selectivity, as compared to the unsteamed catalyst. Another surprising feature of the use of steamed zeolites of the present invention, is that there is no rapid, initial catalyst deactivation, which is experienced with the unsteamed zeolite.

Experimental

Testing was performed at atmospheric pressure in a glass microreactor. Each catalyst was pretreated at 1000° F. in air to remove moisture followed by $H_2$ pretreatment at 900° F. for 15 minutes. The dodecane charge was pretreated by percolation over activated alumina. All reactions were run at 450° F., 1.36 WHSV, with a $H_2$/HC ratio of 20:1. On line product analysis was performed.

The effects of different steaming procedures upon the cracking selectivity are shown in the following table.

TABLE 3

| | CRACKING SELECTIVITY OVER FRESH AND STEAMED ZSM-5 (T = 120 Min). | | | |
|---|---|---|---|---|
| CATALYST | FRESH | SEVERELY STEAMED | MILDLY STEAMED | OPTIMALLY STEAMED |
| Conversion | 29.4 | 27.3 | 36.0 | 46.2 |
| Alpha | 150 | 90 | 320 | 140 |
| $C_1$-$C_4$/Conv. | 30.2 | 27.8 | 28.6 | 25.8 |
| $C_5$-$C_{11}$/Conv. | 69.2 | 71.6 | 70.8 | 73.7 |
| AR./Conv. | 0.61 | 0.67 | 0.55 | 0.43 |
| $C_4$ Iso/N | 0.34 | 0.22 | 0.31 | 0.30 |

In this table, essentially the same starting material was used for all of the ZSM-5 catalyst.

The following table presents a steaming history of the various catalysts.

TABLE 4

| CATALYST | ALPHA | STEAMING CONDITIONS |
|---|---|---|
| fresh | 150 | — |
| severely steamed | 90 | 850° F./8 Hrs/100% Steam |
| optimally steamed | 140 | 850° F./4 Hrs/100% Steam |
| mildly steamed | 320 | 600° F./6 Hrs/100% Steam |

The above examples show that optimally steamed ZSM-5 catalyst, produced in accordance with the present invention, exhibits greater catalyst stability for paraffin hydrocracking. Surprisingly, the optimal steaming treatment of the present invention also results in better gasoline selectivity and overall catalyst activity.

We claim:

1. A process for converting feedstock comprising hydrocarbon compounds to conversion product comprising hydrocarbon compounds of lower molecular weight than feedstock hydrocarbon compounds which comprises contacting said feedstock at conversion conditions with a catalyst comprising one or more metal promoters selected from the group consisting of platinum, iridium, palladium, nickel, zinc, chromium, copper, rare earth metals and mixtures thereof and a zeolite having a silica/alumina mole ratio greater than 12 and a constraint index of 1 to 12, and wherein said catalyst is steamed in its fresh state under controlled conditions of temperature, time and steam partial pressure so as to initially increase the α-activity of said catalyst and produce a steamed catalyst having a peak α-activity, and subsequently reduce the α-activity from said peak α-activity to an α-activity substantially the same as the α-activity of said fresh catalyst and no more than 25% below the initial α-activity of said fresh catalyst.

2. A process according to claim 1 wherein said zeolite exhibits an x-ray diffraction pattern of ZSM-5.

3. A process according to claim 1 wherein said catalyst has said metal promoters included on it prior to the steaming procedure.

4. A process according to claim 1 wherein said catalyst has said metal promoters included on it after the steaming procedure.

5. A process according to claim 1 wherein said silica/alumina ratio is no less than 20.

6. A process according to claim 5 wherein said silica/alumina ratio is about 40.

7. A process according to claim 5 wherein said silica/alumina ratio is about 70.

8. The process of claim 1 wherein said conversion conditions include a hydrogen partial pressure of about 10 to 3000 psia.

9. The process of claim 1 wherein said conversion is conducted in the absence of added hydrogen.

10. A process for catalytically dewaxing a heavy oil stock to provide a catalytically dewaxed oil with reduced wax content which comprises contacting said oil at catalytic dewaxing conditions including a temperature of about 450° to 900° F. in a reaction zone in the presence of hydrogen with a catalyst comprising one or more metal promoters selected from the group consisting of platinum, iridium, palladium, nickel, zinc, chromium, copper, rare earth metals and mixtures thereof and a zeolite having a silica/alumina mole ratio greater than 12 and a constraint index of 1 to 12, and wherein said catalyst is steamed in its fresh state under controlled conditions of temperature, time and steam partial pressure so as to initially increase the α-activity of said catalyst and produce a steamed catalyst having a peak α-activity, and subsequently reduce the α-activity from said peak α-activity to an α-activity substantially the same as the α-activity of said fresh catalyst and no more than 25% below the initial α-activity of said fresh catalyst.

11. A process according to claim 10 wherein said zeolite exhibits an x-ray diffraction pattern of ZSM-5.

12. A process according to claim 10 wherein said catalyst has said metal promoters included on it prior to the steaming procedure.

13. A process according to claim 10 wherein said catalyst has said metal promoters included on it after the steaming procedure.

14. A process according to claim 10 wherein said silica/alumina ratio is no less than 20.

15. A process according to claim 14 wherein said silica/alumina ratio is about 40.

16. A process according to claim 14 wherein said silica/alumina ratio is about 70.

17. The process of claim 10 wherein said metal promoters are selected from the group of platinum, iridium, palladium, nickel and mixtures thereof.

18. Process of claim 10 wherein said feed comprises a lubricating oil base stock.

19. Process of claim 10 wherein said feed comprises a distillate fuel oil.

20. A process for catalytically hydrodewaxing a lubricating oil base stock to provide a catalytically hydrodewaxed lubricating oil base stock with reduced wax content which comprises contacting said stock at catalytic hydrodewaxing conditions including a temperature of about 450° to 900° F. in a reaction zone operating with a hydrogen partial pressure of about 10 to 300 psia with a catalyst comprising one or more metal promoters selected from the group consisting of platinum, iridium, palladium, nickel, zinc, chromium, copper, rare earth metals and mixtures thereof and a zeolite having a silica/alumina mole ratio greater than 12 and a constraint index of 1 to 12, and wherein said catalyst is steamed in its fresh state under controlled conditions of temperature, time and steam partial pressure so as to initially increase the α-activity of said catalyst and produce a steamed catalyst having a peak α-activity, and subsequently reduce the α-activity from said peak α-activity to an α-activity substantially the same as the α-activity of said fresh catalyst and no more than 25% below the initial α-activity of said fresh catalyst, said steamed catalyst having enhanced stability over said fresh catalyst.

* * * * *

UNITED STATES PATENT AND TRADEMARK OFFICE
CERTIFICATE OF CORRECTION

PATENT NO. : 4,594,146

DATED : June 10, 1986

INVENTOR(S) : Arthur W. Chester and Yung-Feng Chu

It is certified that error appears in the above-identified patent and that said Letters Patent is hereby corrected as shown below:

Column 1, line 9, "continuation-in-part" should be --continuation--

Column 10, Claim 20, line 7, "300" should be --3000--

Signed and Sealed this

Thirtieth Day of December, 1986

Attest:

DONALD J. QUIGG

Attesting Officer

Commissioner of Patents and Trademarks